(12) United States Patent
Tsubata et al.

(10) Patent No.: US 9,018,245 B2
(45) Date of Patent: Apr. 28, 2015

(54) METHOD FOR PROMOTING IMMUNE RESPONSE COMPRISING INHIBITING CD22 FUNCTION IN B CELLS

(75) Inventors: Takeshi Tsubata, Kawaguchi (JP); Taishi Onodera, Kawaguchi (JP)

(73) Assignee: Japan Science and Technology, Saitama (JP)

( * ) Notice: Subject to any disclaimer, the term of this patent is extended or adjusted under 35 U.S.C. 154(b) by 563 days.

(21) Appl. No.: 12/516,134

(22) PCT Filed: Dec. 21, 2007

(86) PCT No.: PCT/JP2007/074634
§ 371 (c)(1),
(2), (4) Date: Jul. 24, 2009

(87) PCT Pub. No.: WO2008/078673
PCT Pub. Date: Jul. 3, 2008

(65) Prior Publication Data
US 2010/0063130 A1    Mar. 11, 2010

(30) Foreign Application Priority Data
Dec. 26, 2006   (JP) ................................ 2006-349458

(51) Int. Cl.
| | |
|---|---|
| G01N 33/53 | (2006.01) |
| G01N 33/567 | (2006.01) |
| A61K 39/00 | (2006.01) |
| C12N 5/0781 | (2010.01) |
| G01N 33/50 | (2006.01) |
| C07K 16/00 | (2006.01) |

(52) U.S. Cl.
CPC .............. *A61K 39/00* (2013.01); *C12N 5/0635* (2013.01); *G01N 33/5052* (2013.01); *G01N 2333/70503* (2013.01)

(58) Field of Classification Search
None
See application file for complete search history.

(56) References Cited

U.S. PATENT DOCUMENTS

2004/0176309 A1   9/2004  Kelm et al.

FOREIGN PATENT DOCUMENTS

WO         03/072736        9/2003

OTHER PUBLICATIONS

Abbas et al. Cellular and Molecular Immunology published by Saunders, Fifth Edition 2003, Section I, pp. 20-22.*
Walker et al. Immunology, 2007 123:314-325.*
Supplementary European Search Report of Application No. EP 07 85 1040.
Yu, J et al, "Establishment of the Screening for Mouse CD22 Inhibitors", Proceedings of the Japanese Society for Immunology (2006) 36:178.
Sliedregt, L. A. J. M et al, "Design and Synthesis of a Multivalent Homing Device for Targeting to Murine CD22", Bioorganic & Medicinal Chemistry (2001), 9:85-97.
Haas, K et al, "CD22 Ligand Binding REgulates Normal and Malignant B Lymphocyte Survival in Vivo", The Journal of Immunology (Sep. 2006) 177:3063-3073.
Sokol, D et al, "Antisense and Ribozyme Constructs in Transgenic Animals", Transgenic Research (Jan. 1996), 5 (6): 363-371.
Caplen, NJ, "Gene Therapy Progress and Prospects. Downregulating Gene Expression: the Impact of RNA Interference", Gene Therapy (Aug. 2004) 11(16):1241-1248.
Lewin, A et al, "Ribozyme Gene Therapy: Applications for Molecular Medicine", TRENDS in Molecular Medicine (May 2001) 7(5):221-228.
Nitschke, L et al, "Molecular Interactions Regulate BCR Signal Inhibition by CD22 and CD72", TRENDS in Immunology (Oct. 2004) 25(10):543-550.
Tedder, T. F et al, "A Multifunctional Receptor that Regulates B Lymphocyte Survival and Signal Transduction", Advances in Immunology (Jan. 2005) 88(1):1-50.
Onodera, T et al, "CD22 Regulates Time Course of Both B Cell Division and Antibody Response", The Journal of Immunology (Jan. 2008) 180(2):907-913.
O'Keefe, et al. Hyperresponsive B Cells in CD22-Deficient Mice, Science, 1996, vol. 274, No. 5288, p. 798-801.
Kelm, et al., The Ligand-binding Domain of CD22 is Needed for Inhibition of the B Cell Receptor Signal, as Demonstrated by a Novel Human CD22-specific Inhibitor Compound, Journal of Experimental Medicine, 2002, vol. 195, No. 9, p. 1207-1213.
Wakabayashi, et al., A distinct Signaling Pathway Used by the IgG-containing B Cell Antigen Receptor, Science 2002, vol. 298, No. 5602, p. 2392-2395.
Martin, et al., Burst-enhancing role of the IgG membrane tail as a molecular determinant of memory, Nature Publishing Group, vol. 3, No. 2, 2002, p. 182-188.
Nitschke, et al., Molecular interactions regulate BCR signal inhibition by CD22 and CD72, Elsevier Ltd., vol. 25, No. 10, 2004, p. 543-550.
Tedder, et al CD22, A B Lymphocyte-Specific Adhesion Molecule that regulates antigen receptor signaling, Annu. Rev. Immunology, 1997, vol. 15, p. 481-504.
International Search Report dated Mar. 18, 2008 (International Application No. PCT/JP2007/074634).

* cited by examiner

*Primary Examiner* — Chun Dahle
(74) *Attorney, Agent, or Firm* — Ping Wang; Andrews Kurth LLP (57) ABSTRACT

The purpose of the present invention is to elucidate a relationship between deregulation of signaling by CD22 and a rapid response of B cells by IgG-BCR and the like, and to provide a method capable of inducing a rapid immune response and defending against infection instead of vaccine. The present invention relates to a method for promoting an immune response causing such a strong proliferation of clones and production of a large amount of antibody-producing cells as those seen in the memory immune response even in the naive B cells expressing IgM-BCR and IgD-BCR by inhibiting the CD22 function in B cells; and to a method for screening a substance capable of promoting the immune response based on a change in the CD22 function in B cells.

5 Claims, 7 Drawing Sheets

METHOD FOR PROMOTING IMMUNE RESPONSE COMPRISING INHIBITING CD22 FUNCTION IN B CELLS

FIELD OF THE INVENTION

The present invention relates to a method for promoting immune response comprising inhibiting CD22 function and the like.

BACKGROUND OF THE INVENTION

IgM and IgD positive naive B cells, which reacted with a normal T cell-dependent antigen, will move to splenic red pulp and bridging channel and proliferate there to form extrafollicular foci in an early stage of immune response. Plasmablast will proliferate in the extrafollicular foci and undergo differentiation into antibody-producing cells so as to eliminate an antigen. Most of the antibody-producing cells generated in the early stage will have a short life span, while a part of them will induce class-switching into IgG class and the like. A part of B cells that has reacted with an antigen will proliferate in follicle and form a germinal center. B cells will accumulate point mutations in their immunoglobulin V-region during the germinal center reaction so as to increase their affinity for the antigen. Most of B cells in the germinal center will induce the class-switching. The antibody-producing cells that have gone through the above germinal center reaction will bear the production of antibodies thereafter. A part of B and T lymphocytes that were activated by antigen-stimulation in a first immune response will grow into memory lymphocytes. Memory B cells will be generated from a part of the germinal center B cells. The memory lymphocytes will survive for a long period of time. When being exposed to the same antigen, the memory lymphocytes will proliferate more rapidly than the naive B cells and form a huge foci of plasmablasts and plasma cells in the splenic red pulp and bridging channel, resulting in a rapid and large-scale production of antibodies. Vaccine will defend against infection by inducing immune memory.

B cell antigen-receptor (BCR) consists of a membrane-type immunoglobulin and signal component Igα/Igβ molecules. Upon the reaction with the antigen, BCR will intracellularly transduce a signal through the Igα/Igβ molecules (class II antigen). Coreceptors of BCR such as CD19, CD22, CD72 and FcγR2B modulate an appropriate threshold for signaling by positively or negatively regulating BCR signal transduction (signaling), so that they will have an influence on determination of the fate of B cells such as proliferation, differentiation into the antibody-producing cells, non-response or apoptosis. Among them, CD22 is known as a molecule that will down-modulate the BCR signaling. Three immune receptor tyrosine-based inhibition motifs (ITIM) existing in an intracellular region of CD22 will be phosphorylated directly after BCR crosslinking has occurred, and CD22 will recruit a phosphatase, Src-homology domain 2 (SH2)$^-$ containing protein tyrosine phosphatase-1 (SHP$^-$ 1) near BCR so as to activate it and negatively regulate the BCR signaling.

The memory B cells will be generated through the differentiation mainly from cells that have been class-switched into IgG, and express the membrane-type IgG as the BCR. IgG-BCR will transduce a signal through the Igα/Igβ molecules like IgM-BCR and IgD-BCR expressed by the naive B cells. Recently, a finding has been obtained that the IgG-BCR is involved in the rapid response of the memory B cells (Wakabayashi, C., et al., Science, 2002, 298(5602): p. 2392-5).

Goodnow et al. made a transgenic mouse in which almost all of the B cells expressed IgG specific for HEL, and analyzed an immune response of IgG-positive naive B cells. They revealed that the IgG-positive naïve B cells would rapidly proliferate upon the antigen stimulation similarly in the case of the memory immune response, so that they would form a huge foci of the plasmablast and produce a large amount of antibodies (Martin, S. W. and C. C. Goodnow, *Nat Immunol.* 2002, 3(2): p. 182-8). These results show that the IgG-BCR has a function different from the IgM-BCR or IgD-BCR, and is involved in a rapid activation of B cells in the memory response.

On the other hand, the present inventors found that while the IgM-BCR or IgD-BCR were negatively regulated by CD22, the IgG-BCR would not be regulated by CD22 so that it could induce an effective signaling (Wakabayashi, C., et al., Science, 2002. 298(5602): p. 2392-5).

[Non Patent Document 1] Nitschke, L. and T. Tsubata, *Trends Immunol*, 2004. 25(10): p. 543-50

[Non Patent Document 2] Tedder, T. F., et al., *Annu Rev Immunol*, 1997. 15: p. 481-504.

DISCLOSURE OF THE INVENTION

Problems to be Solved by the Invention

However, it has been unknown how much the release of signal regulation by CD22 is involved in the rapid response of B cells through IgG-BCR, or whether or not the regulation of CD22 function could induce such a rapid antibody-response as that in the memory response.

In order to solve the above problems, the present inventors analyzed in detail kinetics in vivo of NP (nitrophenol)-reactive and CD22-deficient B cells in immune response, which cells were obtained by breeding a CD22-deficient mouse with a QM mouse most of whose B cells were reactive with a hapten, NP. As a result, it has been revealed that there will occur such a strong proliferation of clones and production of a large amount of antibody-producing cells as those seen in the memory immune response even in the naive B cells expressing IgM-BCR and IgD-BCR due to the deficiency of CD22, leading to the completion of the present invention.

Means for Solving Problems

The present invention comprises the following aspects:

[Aspect 1] A method for promoting an immune response comprising inhibiting CD22 function in B cells.

[Aspect 2] A method according to Aspect 1, wherein the B cells are IgM and IgD positive naive B cells.

[Aspect 3] A method according to Aspect 1 or 2, wherein the promotion of the immune response comprises the increase of proliferation, division and/or survival of the B cells in an early stage of the immune response.

[Aspect 4] A method according to Aspect 3, wherein the B cells comprises IgG1$^+$B cells, IgM$^+$ B cells and germinal center B cells.

[Aspect 5] A method according to Aspect 1 or 2, wherein the promotion of the immune response comprises class switching and/or differentiation of the B cells in an earlier stage.

[Aspect 6] A method according to Aspect 5, wherein the class switching is that to the IgG1$^+$ positive cells, and/or the differentiation is that into antibody-producing cells or the germinal center B cells.

[Aspect 7] A method according to any one of Aspects 2-6, wherein the early stage in the immune response means from the third to fifth days after the immunization.

[Aspect 8] A method according to Aspect 1, wherein the promotion of the immune response comprises an increase in a number of the antibody-producing cells and in the amount of antibodies produced, and/or the production of antibodies in an earlier stage.

[Aspect 9] A method according to Aspect 8, wherein the antibodies produced in the earlier stage are IgG and/or IgM.

[Aspect 10] A method according to any one of Aspects 1-9, wherein the inhibition of the CD22 function is caused by its dysfunction due to deficiency or mutation of CD22 gene.

[Aspect 11] A method according to any one of Aspects 1-9, wherein the inhibition of the CD22 function is caused by repression of the expression of CD22 gene.

[Aspect 12] A method according to Aspect 11, wherein the repression of the expression of CD22 gene is done at a transcriptional level.

[Aspect 13] A method according to Aspect 12, wherein gene knockdown by means of siRNA specific for CD22 gene is used.

[Aspect 14] A method according to Aspect 13, wherein the siRNA is a double strand RNA consisting of an oligonucleotide having 21-23 bases and its complementary oligonucleotide, which comprises a continuous base sequence of a part of CD22 gene.

[Aspect 15] A method according to any one of Aspects 1-9, wherein the inhibition of the CD22 function is related to the inhibition of signal transduction of B cell receptor.

[Aspect 16] A method according to any one of Aspects 1-15, wherein the B cells and/or the CD22 or CD22 gene is derived from a mouse.

[Aspect 17] B cells whose CD22 function is inhibited.

[Aspect 18] B cells according to Aspect 17, which are isolated from a knockout animal wherein CD22 gene is knocked out.

[Aspect 19] A method for the production of an antibody using the method according to any one of Aspects 1-15 or the B cells whose CD22 function is inhibited according to Aspect 17 or 18.

[Aspect 20] A method for the production according to Aspect 19, wherein the antibody is specific for a T cell-dependent antigen.

[Aspect 21] A method for screening of a substance capable of promoting the immune response based on a change in the CD22 function in the B cells.

[Aspect 22] A method for screening according to Aspect 21, comprising the following steps:
(a) a step of contacting a substance to be screened with the B cells;
(b) a step of detecting the CD22 function in said cells; and
(c) a step of selecting a substance which inhibits said function.

[Aspect 23] A method for screening according to any one of Aspect 19-22, wherein the B cells and/or the CD22 or CD22 gene is derived from a mouse.

[Aspect 24] A screening kit used in a method according to any one of Aspects 21-23.

Advantages of the Invention

It has been first revealed by the present invention that the immune response can be promoted by inhibiting or repressing the CD22 function in the B cells. According to the present invention, such a strong proliferation of clones and a mass production of the antibody-producing cells as those seen in the memory immune response can be effected even in the naive B cells expressing IgM-BCR and IgD-BCR, by inhibiting the CD22 function. These results suggest that a rapid activation of the B cells will occur in the memory immune response since the signaling mediated by IgG-BCR expressed in the memory B cells is not inhibited by CD22, showing the possibility to defend against infection by inducing the rapid immune response instead of a vaccine.

Best Mode for Carrying Out the Invention

According to the present invention, the promotion of the immune response was effected by inhibiting (or, repressing) the CD22 function in the B cells. Although the term "B cells" used in the present specification usually means IgM and IgD positive naïve B cells (mature B cells), it is not limited to these types and comprises B cells that potentially have capability of differentiating into antibody-producing cells in response to the T antigen-dependent antigen. Furthermore, in the present specification, various kinds of cells including the B cells and the CD22 (gene) may be derived from any animal cells known for those skilled in the art, including mammals such as humans and mice.

The promotion of the immune response according to the present invention comprises any reaction known to those skilled in the art, for example, the increase in proliferation and survival of the B cells in an early stage of the immune response, especially, the increase of in the proliferation, division and/or survival of the B cells, such as the increase in numbers of the $IgG1^+$B cells; the $IgM^+$ B cells and the germinal center B cells by a factor of two to three compared to the $CD22^{+/+}$ B cells; the class switching of the B cells into the $IgG1^+$ positive cells, and/or differentiation in an earlier stage into, for example, the antibody-producing cells or the germinal center B cells; the increase in the number of cells producing antibodies such as IgG and/or IgM in immune organs such as spleen, and in an amount of the antibodies produced in serum (about three to five times more than that of $CD22^{+/+}$ B cells), and/or the production of these antibodies in an earlier stage, and the promotion of signal transduction through the B cell receptor.

The "early stage in an immune response" usually means a few days, such as, from the third to the fifth days after the immunization (stimulation or sensitization by an antigen), with a variation of about one or two days depending on the kind of an antigen used as an immunogen, and aspects in the promotion of the immune response and the like.

The inhibition of the CD22 function in the B cells may be carried out by any genetic (genomic) engineering technique or method known for those skilled in the art. As long as the immune response is significantly promoted, it is not necessary to completely inhibit the CD22 function.

The inhibition of the CD22 function may be caused by any action on the CD22 gene per se, such as by dysfunction due to deficiency or mutation of the CD22 gene. Such action on the gene per se may be effected by, for example, knockout of the CD22 gene by means of gene targeting technique known for those skilled in the art, or introduction of mutation into the gene by means of various methods for that so as to express CD22 variant not having a prescribed function.

The inhibition of the CD22 function may be caused by repression of the expression of the CD22 gene, which may be done at any optional level such as a transcriptional level.

For example, the repression of the expression of the gene at the transcriptional level may be done by gene knockdown by means of a nucleic acid sequence inducing RNA interference (RNAi) against the CD22 gene (DNA or mRNA) (a single or double stranded RNA having a sequence specific for a partial sequence of said gene, such as siRNA); antisense RNA; or various ribozymes.

The nucleic acid sequence inducing the RNA interference against the CD22 gene may be optionally designed and prepared by those skilled in the art, based on a base sequence of the CD22 gene registered in any known public database, such as accession No. L16928 GenBank/EMBL/DDBJ for mouse CD22 gene. The siRNA is a double strand RNA consisting of an oligonucleotide having 15-30, especially 21-23 bases and its complementary oligonucleotide, which comprises a continuous base sequence of a part of the CD22 gene. The siRNA may comprise one that will be intracellularly generated upon digestion by Dicer.

It is also possible to inhibit the CD22 function at the transcriptional level by manipulating a transcriptional-regulating region of the CD22 gene so as to inhibit its normal transcription.

Furthermore, it is possible to inhibit the CD22 function by expressing a substance that will inhibit the CD22 function at any stage with any transformation method known to those skilled in the art.

The CD22 function may be inhibited in the B cells in vivo or in vitro. In vivo, such inhibition may be effected by producing a knock-out animal such as a mouse whose CD22 gene has been knocked out.

Accordingly, the present invention also relates to B cells (population) that the CD22 function is inhibited. Such cells may be prepared by isolating $CD23^+$ follicle cells by means of any sorting technique known to those skilled in the art from the spleens cells derived from the above knock-out animal or mammal such as the knock-out mouse, or a mammal such as mouse that is genetically related to them (for example, animals such QM mice as described in the Example in the present specification, which are obtained by being bred with other animals such as a mouse that will react with a particular antigen (hapten)). An example of the above B cells is a spleen cell (IgHa, Ly5.2) of $CD22^{-/-}$QM mouse prepared in Example 1. Alternatively, it is possible to easily prepare the B cells (population) that the CD22 function is inhibited by using any one of the above genetic engineering techniques. Furthermore, it is possible to obtain the B cells whose CD22 function is inhibited, by knocking out the CD22 gene in various stem cells such as ES cells, and differentiating them into B cells.

The above B cells whose CD22 function is inhibited may be used not only in the method according to the present invention, but also utilized effectively in methods for the analysis of the immune response, or for screening a substance capable of promoting an immune response.

The present invention is also related to a method for the production of an antibody using any one of the above methods or the above B cells whose CD22 function is inhibited. The antibody may be prepared by using any method or technique known to those skilled in the art for any antigen such as a T cell-dependent antigen.

Since the immune response will be promoted by inhibiting the CD22 function as already described, it will be possible to screen a substance capable of promoting the immune response, for example, based on a change in the CD22 function in the B cells. Accordingly, the present invention also relates to such screening method and a screening kit used in the method.

One example of the screening method according to the present invention comprises the following steps:
(a) a step of contacting a substance to be screened with the B cells;
(b) a step of detecting the CD22 function in said cells; and
(c) a step of selecting a substance which inhibits said function.

The change (inhibition) of the CD22 function may be directly detected by determining a degree of inhibition of the expression of the CD22 gene at any stage such as transcription and translation with any method known for those skilled in the art.

An amount of the expression of the CD22 gene may be determined by an amount of its mRNA in the above screening method. The determination of mRNA may be carried out by any methods known to those skilled in the art such as various quantitative PCR methods such as RT-PCR and micro array (DNA chip) using primers designed optionally based on a base sequence of the gene encoding CD22 protein. Alternatively, the change (inhibition) of the CD22 function may be indirectly detected by detecting various aspects involved in the promotion of the immune response by the inhibition of the CD22 function as already described.

The cells such as the B cells and/or the CD22 or CD22 gene used in the screening method according to the present invention may be derived from any known animal including mammals such as mice and humans. The screening may be carried out in vivo or in vitro. In vitro, for example, the B cells may be contacted with the substance to be screened by culturing the cells in the presence of said substance. In vivo, the B cells may be contacted with the substance to be screened in a body by administrating said substance into an experiment animal with a suitable method.

The kit used in the screening method according to the present invention may be optionally constituted depending on specific mechanism on detection and determination of the CD22 function in B cells and the like. The kit may comprises, for example, an agent comprising an antibody specifically recognizing CD22 protein, primers for amplification of the CD22 gene and a probe for hybridization, which may have a suitable length, for example, of a base sequence having continuous 10-100 bases depending on their use.

The above primers, probe and antibody comprised in the above kit as a constituent may be labeled with a suitable labeling substance such as a radioactive material, fluorescent material, pigment and the like. The kit may further comprise any other elements or components known to those skilled in the art such as various agents, enzymes, buffers, a reaction plates, etc. depending on its structure and purpose for use.

As already described, the cells such as the 8 cells and/or the CD22 or CD22 in the present specification may be derived from any known animal including mammals such as mice and humans. The information about these genes is known for those skilled in the art, and may be easily obtained from various public databases (cf. GenBank/EMBL/DDBJ, accession No. X59350).

DNAs (genomic DNA and cDNA) encoding CD22, according to the present invention, include in addition to DNA having the above specific base sequence (nucleotide sequence) a DNA hybridizing under stringent conditions with a DNA consisting of a base sequence complementary with that of the above DNA, and a DNA consisting of a base sequence showing identity (homology) of about 80% or more, preferably about 95% or more with that of the above DNA, which encode a protein substantially having at least one of the CD22 functions.

The hybridization may be performed in accordance with a method known in the art, for example, that described in Molecular cloning third ed. (Cold Spring Harbor Lab. Press 2001) or in Current protocols in molecular biology (edited by Frederick M. Ausubel et al., 1987). When a commercially available library is used, the hybridization may be done according to instructions attached to it.

The term "stringent conditions" means in this specification, for example, those of sodium concentration of 15~900 mM, preferably 15~600 mM, more preferably 15~150 mM, pH of 6~8 at 60° C.~68° C.

Thus, the DNA that may hybridize with DNA consisting of the base sequence complementary with that of the DNA consisting of the above base sequence may include, for example, a DNA comprising a base sequence having identity of about 80% or more, preferably of about 95% or more, and more preferably of about 99% or more on a total average with the whole base sequence of the DNA of interest.

The above DNAs may be obtained by PCR, for example, using suitable primers prepared in the information about the base sequence disclosed in Non Patent Document 1 or in the present specification. The DNA according to the present invention may be also prepared by chemical synthesis.

The CD22 protein according to the present invention may include a polypeptide having an amino acid sequence wherein one or a few amino acids are deleted, substituted or added with respect to an amino acid sequence encoded by the above base sequence, which substantially has at least one of the CD22 functions.

In order to determine the identity of sequences between two amino acid sequences or two nucleotide (base) sequences, the sequences will be pre-treated to become in an optimum condition for comparison. For example, gaps may be inserted into one of the sequences so that alignment with the other sequence will be optimized. After such pre-treatment, amino acid residues or bases in each region will be compared. When amino acid residues or bases located at a certain position in a first sequence are the same as those of a second sequence located at a position corresponding to the above position in the first sequence, these two sequences will be considered as the same at the position. Identity between the two sequences will be shown by percentage of the number of the amino acid residues or bases that are the same in the two sequences for the number of the whole amino acid residues or bases.

According to the above principle, identity between the two amino acid sequences or nucleotide sequences may be determined, for example, by algorithm of Karlin and Altschul (Proc. Natl. Acad. Sci. USA 87:2 264-2268, 1990; and Proc. Natl. Acad. Sci. USA 990:5873-5877, 1993). BLAST or FASTA programs based on the above algorithms may be used for searching a sequence having a high identity with a given sequence from database. Such programs are available at a Web site of National Center for Biotechnology Information on the Internet.

The DNA showing the above identity in the amino acid sequence or nucleotide sequence may be obtained by resorting to the above hybridization, or may be easily found in public databases or a group of functionally unidentified DNAs obtained with an analysis of genome sequences by means of methods conventionally used by those skilled in the art; for example, by searching with the above BLAST software.

The present invention will be further explained by the following examples, which do not limit the scope of the present invention. The genetic procedures in the examples are done in accordance with any standard techniques in gene engineering and molecular biology such as those described in Sambrook and Maniatis, in Molecular Cloning—A laboratory Manual, Cold Spring Harbor Laboratory Press, New York, 1989: Ausbel, F. M. et al., Current Protocols in Molecular Biology, John Wiley & sons, New York 1995. The disclosure cited in the present specification as a whole will constitute a part of the present specification.

Example 1

Figure 1:
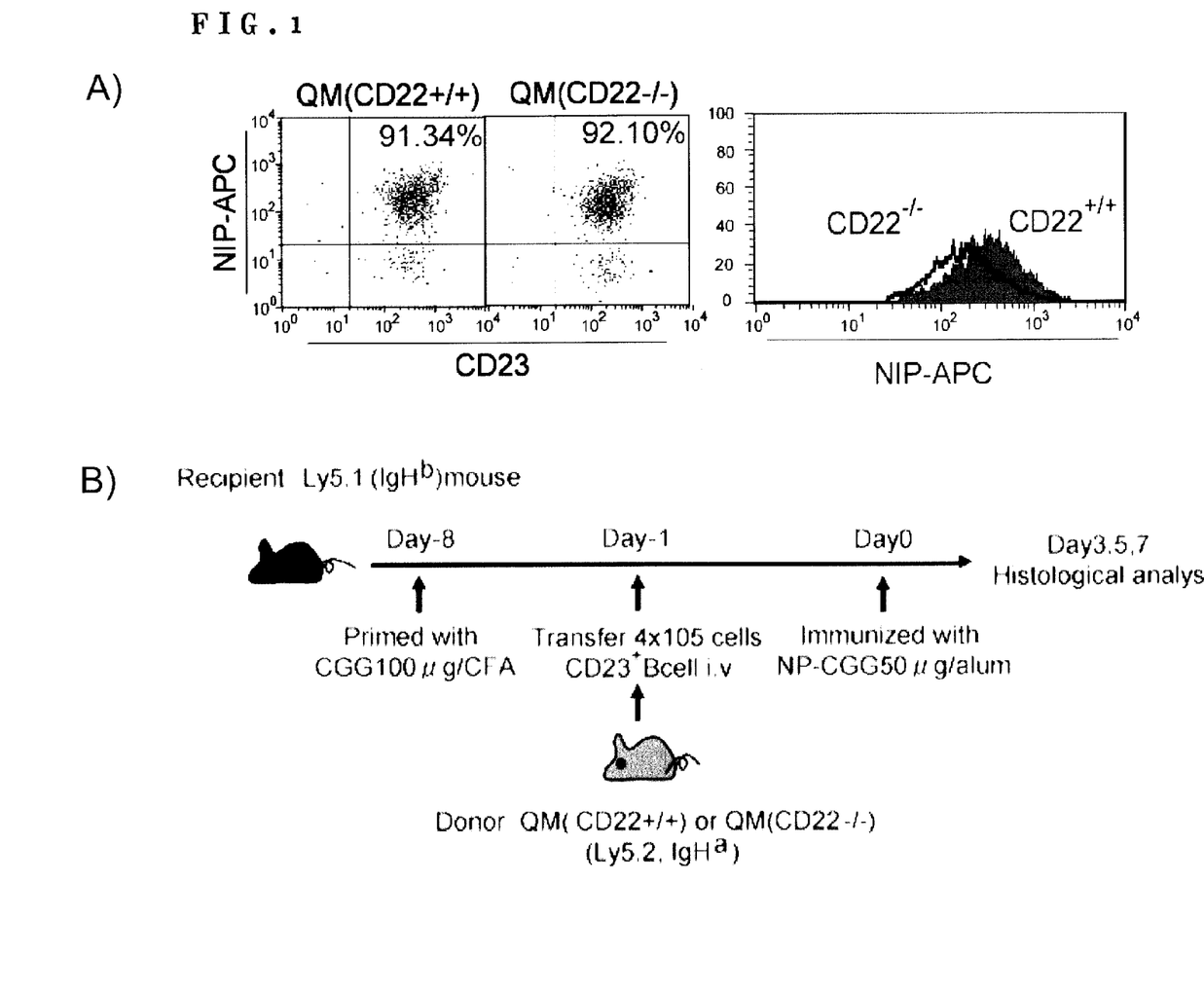
FIG. 1 shows the occurrence of a burst of extrafollicular plasmablast in CD22 deficient B cells in the early stage of immune response. (A) Flow cytometry analysis of isolated B cells, showing the percentage of CD23$^+$ and NIP-reactive SCR$^+$ B cells (left) and an expression amount of NIP-reactive BCR in a histogram (right). (B) A protocol of adopted transfer. (C) Spleen tissue sections observed with a confocal fluorescence microscope, showing that the burst of the extrafollicular plasmablast occurred in the CD22 deficient B cells in the early stage of the immune response.

Burst of Extrafollicular Plasmablast of CD22-Deficient B Cells in an Early Stage of Immune Response In order to reveal kinetics of the CD22-deficient B cells that have reacted with an antigen in the immune response, the CD22-deficient QM mouse ($CD22^{-/-}$QM mouse) was prepared by breeding the QM mouse, most of whose B cells will react with nitrophenol (NP), with the CD22-defficient mouse provided Duke University. Among the B cells, follicle B cells are involved in the reaction against the T cell-dependent antigen. Accordingly, spleen cells (IgHa, Ly5.2) of the $CD22^{-/-}$ QM mouse and the $CD22^{+/+}$QM (QM mouse without deficiency of CD22) were stained with PE-labeled anti-CD23 antibody (Cat No. 12-0232-85:e-Bioscience) and Magnet beads-labeled anti-PE antibody (Mat. No. 120-000-294: Miltenyi biotec), followed by positive sorting with Auto MACS to obtain NP-reactive CD23+ follicle B cells (FIG. 1A). An amount of the surface immunoglobulin (BCR) specific for NP expressed in the $CD22^{-/-}$ B cells is half that in the $CD22^{+/+}$ B cells (FIG. 1A). These results coincide with the report that the expression amount of BCR would decrease in $CD22^{-/-}$cells. The CD22-defficient mouse is available from Core F of Consortium for Functional Glycomics (CFG) or Jackson Laboratory (600 Main Street Bar Harbor, Marine 04609 USA), whose original publication name is mSiglec-2; Colony Code Name:CD22.

The follicle B cells ($4 \times 10^5$ per mouse) prepared in the above were administered by an intravenous injection into C57BL/6 Ly5.1 congenic mice (IgHb, Ly5.1) primed in advance with CGG (100 μg) and CFA adjuvant in order to activate helper T cells (Day −1). In the next day (Day 0), the mice were immunized with the T cell-dependent antigen, NP-CGG (50 μg) and alum adjuvant. On the third, fifth and seventh days after the immunization, spleen tissue sections from the recipients transplanted with the $CD22^{-/-}$ QM B cells and the $CD22^{-/-}$ QM B cells, respectively, were stained with an anti-CD38 antibody (Blue) (Cat.No. 12-0381-81:e-Bioscience), an anti-IgM$^a$ antibody (Cat.No. 553515:BD PharmMingen) ((a)-(f)), an anti-IgG1$^a$ antibody (Green)(Cat. No. 553500:BD Pharmingen) ((g)-(l)), or a NIP-APC (Red), and observed with the confocal fluorescence microscope (FIG. 1C). The follicle B cells originated in the recipients were stained only with the anti-CD38 antibody, while the B cells derived from Donors were stained with the anti-IgM$^a$ antibody, the anti-IgG1$^a$ antibody and the NIP-APC. Burst derived from the B cells of $CD22^{-/-}$ Donor was found in the Bridging Channel (arrow) and splenic red pulp (arrowhead).

The results showed that while a small number of the Donor-derived B cells were scattered in the boundary between the follicle B cells and T cell region in the mice transplanted with $CD22^{+/+}$ B cells on the third day after the immunization, proliferation of a large number of the B cells was observed in the same region of the mice transplanted with the $CD22^{-/-}$ B cells, most of which were IgM-positive B cells. While only a small amount of plasmablast was increased in the $CD22^{+/+}$ B cells in Bridging Channel on the fifth day after the immunization, the $CD22^{-/-}$ B cells showed an explosive increase of plasmablast both in the Bridging Channel and splenic red pulp, most of which were found to be class-switched into IgG1. In either the $CD22^{-/-}$ B cells or the $CD22^{+/+}$ B cells, most of the B cells were found in the follicle B cells or the germinal center on the seventh day after the immunization, with only a few plasma cells in the splenic red pulp but no a cluster of such plasmablast as found on the fifth day after the immunization.

The above result showed that the $CD22^{-/-}$ B cells could produce a large amount of plasmablast in such an early stage as on the fifth day after the immunization. This is very similar to the phenomenon that memory B cells would produce a large amount of plasmablast in an early stage of the secondary immune response, and in common with extrafollicular proliferative burst observed on the fifth day in the immune response of IgG transgenic B cells, as reported by Goodnow et al. These results showed that deregulation of the signaling by CD22 would induce such an explosive proliferation as found in the memory immune response. Four mice used in each group were analyzed to give the same result.

Example 2

Rapid Clone-Proliferation and Sustention of Survival of $CD22^{-/-}$ B Cells After Reaction with an Antigen The mechanism of the proliferation of a large amount of plasmablast found in the early stage of the immune response of $CD22^{-/-}$ B cells was then studied. It was known that B cells that had reacted with a hapten NP during the immune response would induce class-switching from IgM mainly into IgG1, and that the germinal center B cells would be produced in response to the T cell-dependent antigen. Accordingly, after the $CD22^{-/-}$ B cells and the $CD22^{+/+}$ B cells ($4 \times 10^5$ cells each) were transplanted into the recipient mice, and the numbers of the total B cells, the IgM-positive B cells, the IgG1-positive B cells or the germinal center B cells, which were derived from the Donor, were counted with the flow cytometry.

Figure 2:
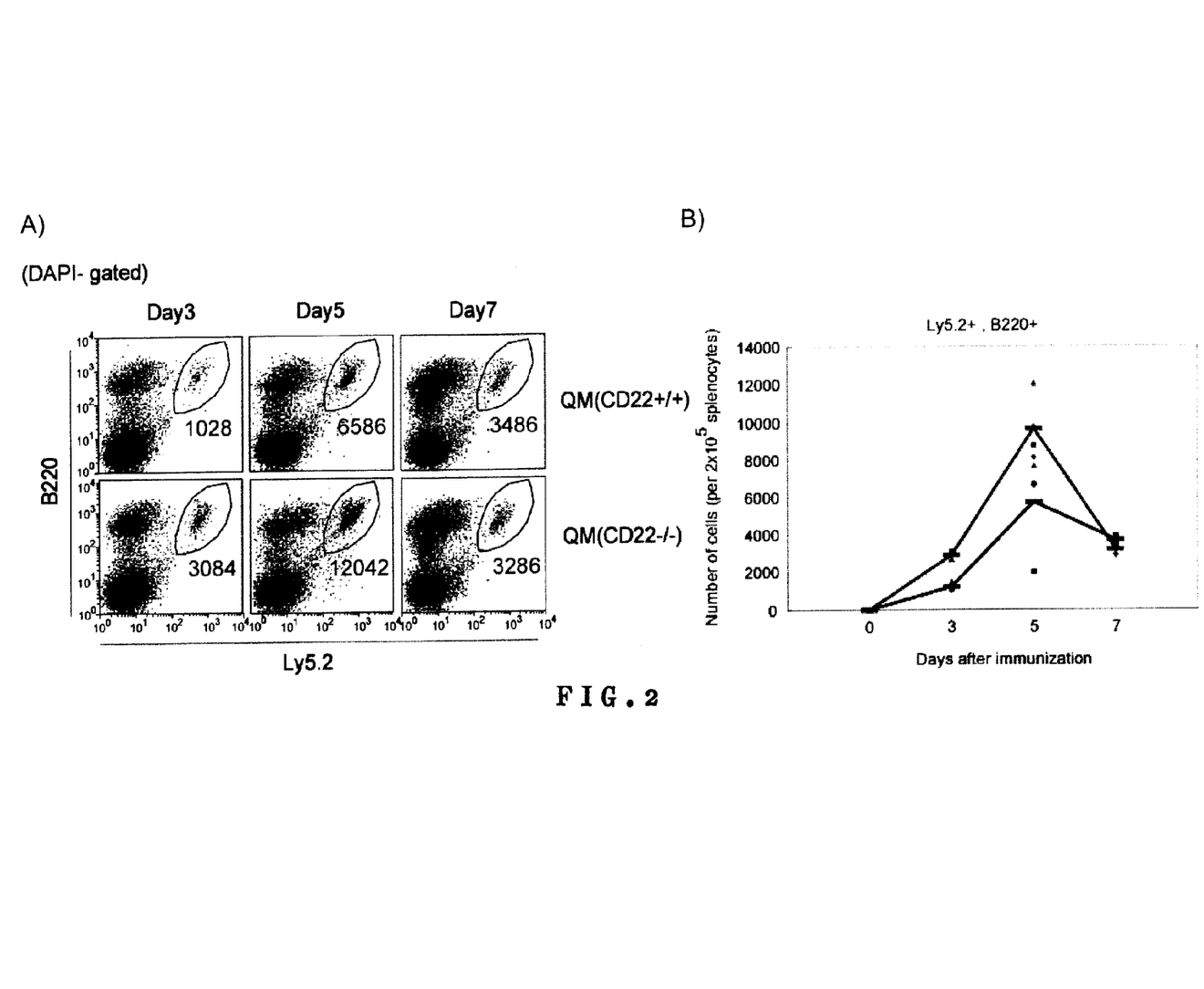
FIG. 2 shows the results obtained with flow cytometry analysis. Spleen cells were collected from the recipient mice that were transplanted with B cells of CD22$^{+/+}$QM (lower polygonal line) and B cells of CD22$^{-/-}$QM (upper polygonal line), respectively, on the third, fifth and seventh days after the immunization. The expression of B220 (A-F), Ly5.2 (A-F), IgM (C) and IgG1 (D), and NIP and PNA reactiveness (E, F) were analyzed. Dead cells were stained with DAPI and excluded from analysis. In spleen cells (DAPI-, 2×10$^5$) of the recipient mice, the numbers of the B cells derived from Donor (B220$^+$, Ly5.2$^+$) (A, B in FIG. 2), the IgM$^+$ B cells derived from Donor (B220$^+$, Ly5.2$^+$, IgM$^+$) (C in FIG. 2), the IgG1$^+$ B cells derived from Donor (B220$^+$, Ly5.2$^+$, IgG1$^+$) (D in FIG. 2), and the germinal center B cells derived from Donor (B220$^+$, Ly5.2$^+$, reactive with NIP and PNA) F in FIG. 2) were counted, respectively. An average of 4 individuals in each group is shown as a bar.

It was found that in both the $CD22^{-/-}$ and $CD22^{+/+}$ QM B cells, all of the total B cells, the IgM-positive B cells, the IgG1-positive B cells and the germinal center B cells had been increased until the fifth day after the immunization, and then decreased on the seventh day after the immunization (FIG. 2). There was a tendency that the IgG1-positive B cells would increase a little bit more late than the IgM-positive B cells would (FIG. 2D). At a peak time on the fifth day after the immunization, the number of the $CD22^{-/-}$ QM B cells increased about twice or three times as much as that of the $CD22^{+/+}$ QM B cells with respect to all of the total B cells, the IgM-positive B cells, the IgG1-positive B cells and the germinal center B cells (FIG. 2E, F). On the other hand, the number of the $CD22^{-/-}$ QM B cells more drastically dropped on the seventh day after the immunization than that of the $CD22^{+/+}$ QM B cells did, down to the same level as the $CD22^{+/+}$ QM B cells. Thus, it was revealed that the $CD22^{-/-}$ QM B cells increased more than the $CD22^{+/+}$ QM B cells did in the early stage of the immune response in each of the sub-populations of the IgM$^+$ B cells, the IgG1$^+$ B cells and the germinal center B cells.

Figure 3:
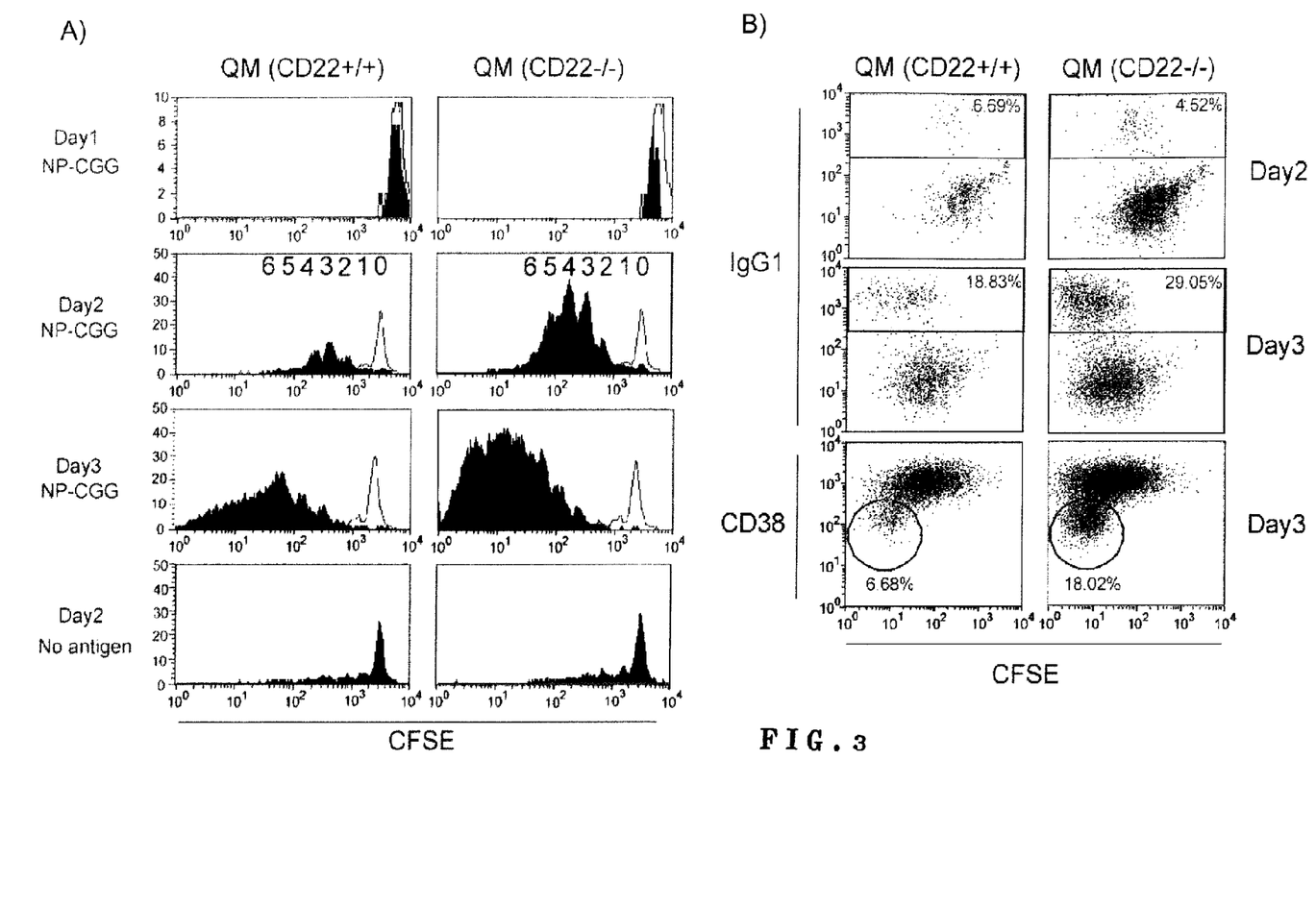
FIG. 3 shows the results of the proliferation of the Donor B cells, class-switching and differentiation into the germinal center B cells, obtained with flow cytometry analysis. (A) Division of the B cells. As a negative control, only PBS was injected after the transportation of the B cells, and analyzed on the second day after the injection (the lowest figures). Dead cells were stained with DAPI and excluded from analysis, and the results of analysis of spleen cells (DAPI$^-$, 2×10$^5$) of each recipient mouse were shown. The experiment was carried out twice giving the same results. (B) Ig class-switching dependent on cell division and differentiation into the germinal center B cells. Percentages of the IgG1$^+$ B cells (upper and middle) and the germinal center B cells (lower) were shown, respectively. Dead cells were stained with DART and excluded from analysis, and the results of analysis of spleen cells (DAPI$^-$, 2×10$^5$) of each recipient mouse were shown. The experiment was carried out twice giving the same results.

In order to further study the mechanism of increase of the $CD22^{-/-}$ QM B cells, CD23 positive $CD22^{+/+}$ QM B cells and $CD22^{-/-}$ QM B cells were stained with CFSE, and C57BL/6Ly5.1 mice were transplanted with $4 \times 10^6$ cells of each group and immunized with NP-CGG. The proliferation of the Donor B cells, the class-switching and differentiation into the germinal center B cells was observed with the flow cytometry (FIG. 3). The proliferation of Donor B cells was detected by a fluorescence intensity of CFSE of IgM$^+$ B cells (B220$^+$, Ly5.2$^+$, IgM$^+$) derived from the donor on the first, second and third days after the immunization. The class-switching was analyzed based on a fluorescence intensity of CFSE and IgG1 production of the B cells (B220$^+$, Ly5.2$^+$) derived from the donor on the second and third days after the immunization. The differentiation into the germinal center B cells was analyzed based on a fluorescence intensity of CFSE and CD38 expression of the B cells (B220$^+$, Ly5.2$^+$) derived from the donor on the third day after the immunization.

On the first day after the immunization, cells that had decreased in CFSE fluoresce were not detected either in the CD22$^{-/-}$ B cells or the CD22$^{+/+}$ B cells, showing that no cell proliferation occurred. On the second day after the immunization, many cells that had decreased in CFSE fluoresce were observed in both the CD22$^{-/-}$ B cells and the CD22$^{+/+}$ B cells, showing that division of these cells had occurred. However, while the CD22$^{+/+}$ B cells had suspended in the fourth cell division stage, the CD22$^{-/-}$ B cells had already passed fifth or sixth cell division stage on the second day. Furthermore, while a peak of cell division of the CD22$^{+/+}$ B cells occurred in the third cell division stage, that of the CD22$^{-/-}$ B cells occurred in the fourth cell division stage, demonstrating that the cell division of the CD22$^{-/-}$ B cells occurred rapidly in the early stage of the immune response. Furthermore, height of the peak in each cell division stage was higher in the CD22$^{-/-}$ B cells than in the CD22$^{+/+}$ B cells, showing the increase in survival of the CD22$^{-/-}$ B cells, too. On the third day after the immunization, CFSE fluorescence intensity was decreased more significantly in the CD22$^{-/-}$ B cells than in the CD22$^{+/+}$ B cells, showing that the CD22$^{-/-}$ B cells were dividing more rapidly than the CD22$^{+/+}$ B cells were. Since no cell division was observed in the mice that had not immunized after the transplantation of the donor B cells, it was clear that the above cell proliferation was an antigen-specific reaction.

The emergence of the IgG1-positive cells and differentiation into the germinal center B cells were analyzed together with the detection of CFSE fluorescence. It was found that the IgG1-positive cells started to show up in the third cell division stage in both the CD22-/- cells and the CD22$^{+/+}$ B cells. On the third day after the immunization, the IgG1-positive cells derived from the CD22$^{-/-}$ B cells had increased about twice as much as that derived from the CD22$^{+/+}$ B cells. As both the CD22$^{-/-}$ B cells and the CD22$^{+/+}$ B cells had shifted into the germinal center B cells (CD38$^{lo}$) from the seventh or eighth cell division stage, the germinal center B cells derived from the CD22$^{-/-}$ B cells had increased about three times as much as that derived from the CD22$^{+/+}$ B cells (FIG. 3B). No difference was found with respect to the number of cell division that is necessary for differentiation. It may be conceived that more IgG1-positive cells and germinal center B cells were generated from the CD22$^{-/-}$ B cells than from the CD22$^{+/+}$ B cells since the cell division was increased in the CD22$^{-/-}$ B cells.

Example 3

Figure 4:
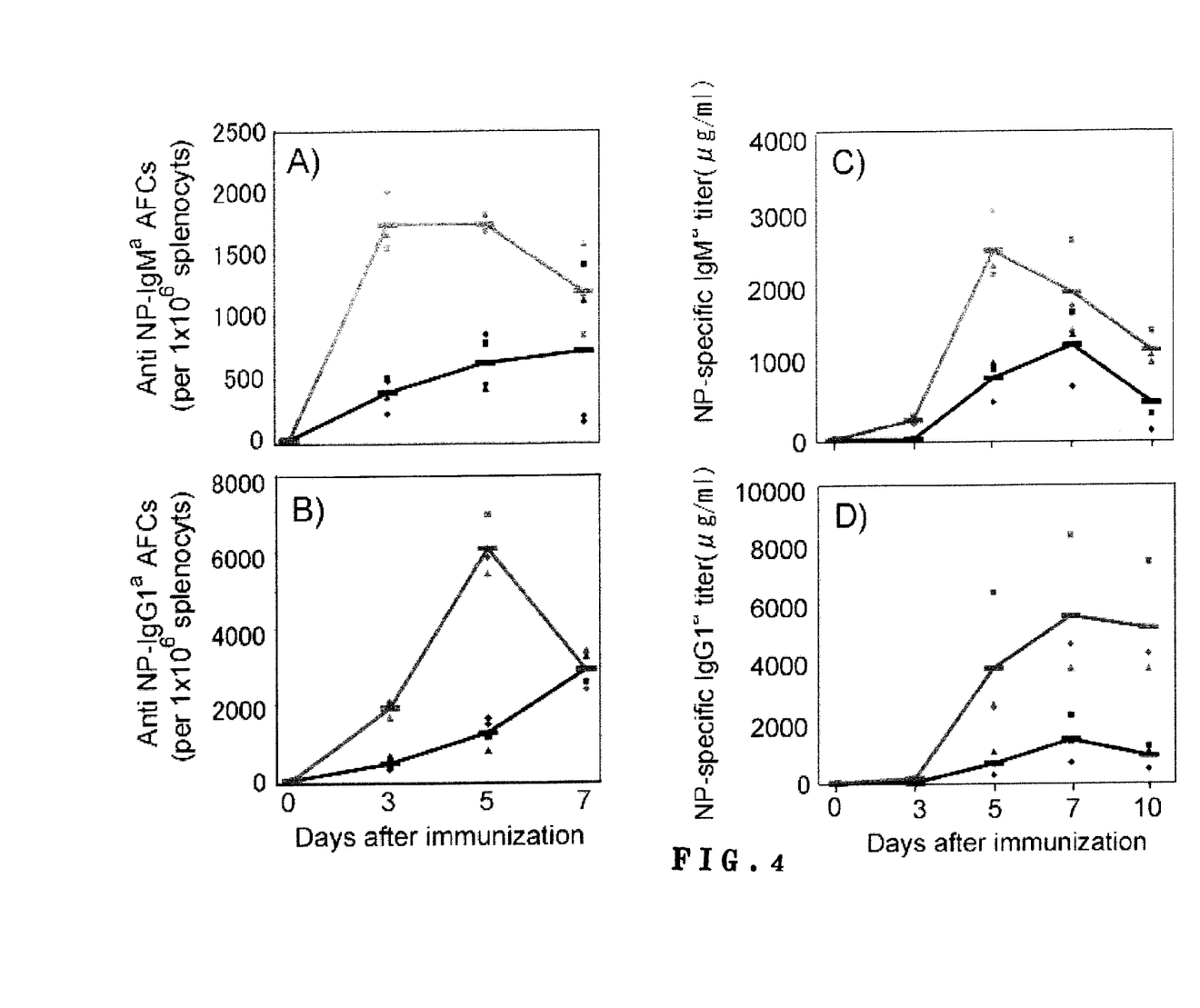
FIG. 4(A, B) shows the number of antibody-producing cells in spleen. Spleen cells were collected from the recipient mice that were transplanted with the B cells of CD22$^{+/+}$QM (lower polygonal line) and the B cells of CD22$^{-/-}$QM (upper polygonal line), respectively, on the third, fifth and seventh days after immunization. Among all of the spleen cells (1×10$^6$), the numbers of cells derived from the Donor B cells, which were producing IgMa antibody (A) and IgG1a antibody (B) specific for NP, were determined by the ELISPOT method. An average from of 4 individuals in each group is shown as a bar. (C, D) Titer of NP-specific antibody derived from the Donor B cells in serum. A production amount (μg/ml) of IgM$^a$ antibody (C) and IgG1a antibody (D) specific for NP in serum of the recipient mice, which were derived from the B cells of CD22$^{+/+}$QM (lower polygonal line) and the B cells of CD22$^{-/-}$QM (upper polygonal line), respectively, was determined by the ELISA method. An average of 4 individuals in each group is shown as a bar.

Production of a Large Amount of Antibody-Producing Cells and Antibodies by CD22$^{-/-}$ B Cells in the Early Stage of the Immune Response As a significant burst of plasmablast of the CD22$^{-/-}$ B cells was observed in the section of spleen tissue in the early stage of the immune response, antibody production was studied with a mouse transplanted with the CD22$^{-/-}$ B cells. The number of cells derived from the Donor B cells and producing an antibody specific for NP in the spleen of the recipient mice was determined by ELISPOT method on the third, fifth and seventh days after immunization (FIG. 4A, B). From the third day after the immunization, about five times or more as many cells producing antibody of either IgM or IgG1 class were detected in the CD22$^{-/-}$ B cells as in the CD22$^{+/+}$ QM B cells. Even on the fifth day after the immunization, five times or more as many cells producing the antibodies of IgG1 class were detected in the CD22$^{-/-}$ B cells as in the CD22$^{+/+}$ QM B cells. However, the number of the cells derived from the CD22$^{-/-}$ B cells and producing the antibody of either IgM or IgG1 class was decreased on the seventh day after the immunization. On the other hand, the number of the above cells had gradually increased in the case of the CD22$^{+/+}$ B cells, showing difference in their kinetics. These results demonstrated that the antibody-producing cells emerged in the earlier stage in the CD22$^{-/-}$ B cells than in the CD22$^{+/+}$ cells.

Titer of NP-specific antibody derived from Donor B cells in serum was then determined (FIG. 4C,D). Being related to the increase of the antibody-producing cells in spleen, a specific IgM antibody has been detected from the third day from the immunization in the mice transplanted with the CD22$^{-/-}$ B cells, and about three times as many specific antibodies were detected in the fifth day from the immunization in said mice transplanted with the CD22$^{-/-}$ B cells as those in the mice transplanted with the CD22$^{+/+}$ B cells. With respect to the kinetics, a peak was reached on the fifth day in the CD22$^{-/-}$ B cells and on the seventh day in the CD22$^{+/+}$ B cells, respectively, showing that the production of the antibodies occurred in the earlier stage in the case of the CD22$^{-/-}$ B cells (FIG. 4C). Furthermore, the production of the IgG1 class antibodies in the CD22$^{-/-}$ B cells increased more significantly than in the CD22$^{+/+}$ B cells, and the extension of such increase was higher than that with respect to the IgM class antibody. Thus, the IgG1 antibodies had been produced about five times as much in the CD22$^{-/-}$ B cells as in the CD22$^{+/+}$ B cells from the fifth day to tenth day after the immunization (FIG. 4D). From the above results, it was clarified that the CD22$^{-/-}$ B cells underwent differentiation into the antibody-producing cells in the earlier stage so as to produce a larger amount of antibodies than the CD22$^{+/+}$ B cells did.

INDUSTRIAL APPLICABILITY

Once memory immune has been established by vaccine, for example, a rapid immune response including the production of antibodies will occur against invasion of pathogenic microorganisms so as to eliminate them and defend against infection prior to the occurrence of life-threatening infection. If medicine that can induce such an early immune response as the memory immune is developed, it can be used to defend against infection caused by various microorganisms instead of vaccine. Since unlike in the case of vaccine it is not necessary to develop the above medicine for each microorganism, it will be especially useful for unknown infectious diseases. The present invention has demonstrated that the antibodies can be produced in the early stage by inhibiting or repressing the CD22 function, so that it will be possible to develop a universal medicine for defending against infection by targeting CD22.

The invention claimed is:
1. A method of screening for a substance inhibiting that inhibits CD22 expression, comprising:
(a) contacting said substance with cultured IgM or IgD positive naive B cells;
(b) measuring CD22 expression in said naïve B cells following said contacting step;
(c) comparing CD22 expression in step (b) with CD22 expression in control IgM or IgD positive naïve B cells; and

(d) determining whether said substance inhibits CD22 expression in said cultured IgM or IgD positive naive B cells relative to the control naïve B cells; and (e) selecting the substance as a substance that promotes an early stage immune response based on said inhibition of CD22 expression in said cultured IgM or IgD positive naïve B cells relative to the control naïve B cells.

2. The method according to claim 1, wherein the method further comprises the step of measuring proliferation or survival of said B cells.

3. The method according to claim 1, wherein the method further comprises the step of treating the cells with an antigen.

4. The method according to claim 1, wherein the B cells are from a mouse.

5. The method according to claim 1, wherein the B cells are from a human.

* * * * *